United States Patent [19]

Spears

[11] 4,400,827
[45] Aug. 23, 1983

[54] METHOD AND APPARATUS FOR CALIBRATING RAPID SEQUENCE RADIOGRAPHY

[76] Inventor: James R. Spears, 118 Riverway Pkwy., #2, Boston, Mass. 02215

[21] Appl. No.: 321,066

[22] Filed: Nov. 13, 1981

[51] Int. Cl.³ .................... G03B 41/16; G21K 3/00
[52] U.S. Cl. ............................ 378/207; 378/158; 378/159; 378/165
[58] Field of Search ............ 378/207, 158, 159, 162, 378/165

[56] References Cited

U.S. PATENT DOCUMENTS

| | | | |
|---|---|---|---|
| 2,258,593 | 10/1941 | Back | 378/207 |
| 2,426,884 | 9/1947 | Keeffer | 378/207 |

Primary Examiner—Craig E. Church
Attorney, Agent, or Firm—Freilich, Hornbaker, Wasserman, Rosen & Fernandez

[57] ABSTRACT

By moving a wedge (18) within the radiographic field during exposure of an area of interest, steps of the wedge are presented one by one at the same film location over sequential exposures. Wedge steps are thus superimposed over an identical position within the radiographic field, and a correlation may then be made between wedge step thickness and film optical density over successive exposures for calibrating the radiographs. A preferred form of the stepped wedge is circular (FIG. 2). An alternate form is a circular ramp (FIG. 3).

10 Claims, 7 Drawing Figures

METHOD AND APPARATUS FOR CALIBRATING RAPID SEQUENCE RADIOGRAPHY

BACKGROUND OF THE INVENTION

This invention relates to a method and apparatus for calibrating rapid sequence radiography, and particularly, though not limited to, cinematic angiograms.

A need exists for an objective method for accurate quantitation of in vivo coronary arterial stenoses. Such a method not only would be useful in the clinical management of individual patients, but also could demonstrate any potential effect of an intervention in attempting to treat arteriosclerotic coronary artery disease in general.

Single plane coronary cinematic angiograms provide potentially useful information about the luminal dimensions of a coronary artery. However, visual inspection is inadequate in measuring "percent" coronary arterial stenoses from coronary cinematic angiograms because of problems of reproducibility and accuracy. As a result, objective methods have been developed in order to more accurately determine the vessel shadow edge, so that a measure of vessel lumen width as well as vessel edge regularity can be obtained. However, no equally accurate method for determining lumen depth is available.

Although the thickness of contrast material at any point within a coronary artery is a function of depth, and the light intensity through a corresonding point of a radiograph is a function of contrast material thickness, the latter relationship is complex and varies with multiple factors, including characteristics of the x-ray beam, film speed and development, and radio-density distribution of objects in the fluoroscopic field; in addition, there is a spontaneous variation in the relationship with time despite constancy of all other factors. What is required is a standard for objective calibration of film gray scale against contrast material thickness.

Materials fabricated in the shape of wedges or stepped wedges have been used in radiology for multiple purposes, including standardizing exposures and providing a reference of comparison for densitometric measurement of object thickness, object density, etc. Typical of such conventional radiographic standards are disclosed in U.S. Pat. Nos. 2,399,650 to Mayer for determining the thickness of hollow aircraft propellar blades and 3,088,027 to Graham for radiographic examination of tubing. See also U.S. Pat. Nos. 1,953,249 to Michel and 2,426,884 to Kieffer. Such radiographic standards have necessarily been limited to situations wherein the background, over which a wedge is superimposed, is homogenous in thickness across the object plane, so that x-ray intensity through the background is the same for each step of the wedge. However, in clinical situations, variability in tissue thickness across the plane perpendicular to the direction of the x-ray beam usually results in a nonuniform radiographic field over the wedge.

Because of the focal nature of the atherosclerotic process, nonaxisymmetric reductions in luminal cross sections are common. Visual inspection of coronary angiograms is limited primarily to luminal edge detection, and, as a result, enface plaques cannot be quantitated from a single radiographic view. Moreover, even for cylindrical lumens, the error of a derived cross-sectional area estimate is a squared function of the error in diameter measurement.

Utilization of all the image information between luminal edges should increase the accuracy of cross-sectional area estimates beyond that derived from edge identification alone. In addition, successful extraction of such three-dimensional information should yield a rotationally invariant measure of cross-sectional area. However, when the radio-density of an entire radiographic field is inhomogeneous, it is not possible to calibrate film gray scale against object thickness in a conventional manner by incorporation of radiographic standards within the field. Crawford, et al., circumvented this problem by modifying an empirically derived mathematical expression characterizing the photographic response of film as described by S. K. Hilal, "Determination of the blood flow by a radiographic technique, Physical considerations and experimental results," Amer J Roentgen 96: 896, 1966., so that relative arterial cord lengths within a femoral arterial cross section could be calculated accurately from knowledge of film optical densities at zero and saturation exposures as well as over the luminal image and its adjacent background. However, radiographic and film development conditions had to be carefully controlled, and the technique has not been applied to radiographic systems employing an image intensifier.

From the foregoing it is evident that the primary problem which has prevented objective calibration of film gray scale against contrast material quantity, a prerequisite to cross-sectional area determination, is the inhomogeneity of the radiographic field during patient exposure. Consequently, conventional radiographic standards of the type referred to above have not been used. Moreover automatic exposure settings, as commonly used, preclude exposing filming standards at times other than during patient exposure.

SUMMARY OF THE INVENTION

An object of this invention is to provide a method and means for calibrating the gray scale in rapid sequence radiography so that data in the recorded image may be quantified in terms of the gray scale obtained by the caibrating technique. A further object is to standardize radiographic systems, especially systems wherein the radio density of the radiographic field is nonhomogeneous, such as the radio density of biological tissues.

The present invention achieves these objects by providing the equivalent to a homogeneous background, i.e., a constant background, which is achieved by utilizing serial frames of radiograph wherein known increments in depth (thickness) of a radio-dense material are moved over identical background positions.

In accordance with a preferred embodiment of the invention, a ramp or stepped wedge is moved within the radiographic field in synchronism with cinematic exposure of an area (field) of interest. Considering the stepped wedge for ease of discussion, successive steps of the wedge are presented at the same film location during sequential exposures. A different thickness of the stepped wedge is thus superimposed over the same point within the radiographic field during each exposure. A correlation may then be made between wedge thickness and film optical density over successive exposures. This correlation is accomplished by measurements of light intensity over the wedge image at the same point in the field for each frame of the cinematic film, i.e., for each position of the wedge as the cinematic film is advanced, one frame at a time. This establishes a calibration curve relating light intensity to thickness of wedge material over a background of constant thickness. Potential application of this technique is determination of luminal cross-sectional area ratios of adjacent coronary artery segments based upon measured lumen depth, which is defined as the sum of the thickness of contrast material within the lumen (the space in the interior of a tubular structure, such as an artery or the intestine) and its background tissue thickness, determined directly from knowledge of the vessel image and the calibration curve, less background tissue thickness alone, determined indirectly from knowledge of tissue thickness between the vessel edges. For unknown contrast material concentration, relative rather than absolute lumen depths are obtained and are used to plot depth distribution curves of lumen cross sections.

The novel features that are considered characteristic of this invention are set forth with particularity in the appended claims. The invention will best be understood from the following description when read in connection with the accompanying drawings.

PREFERRED EMBODIMENTS OF THE INVENTION

Figure 1:
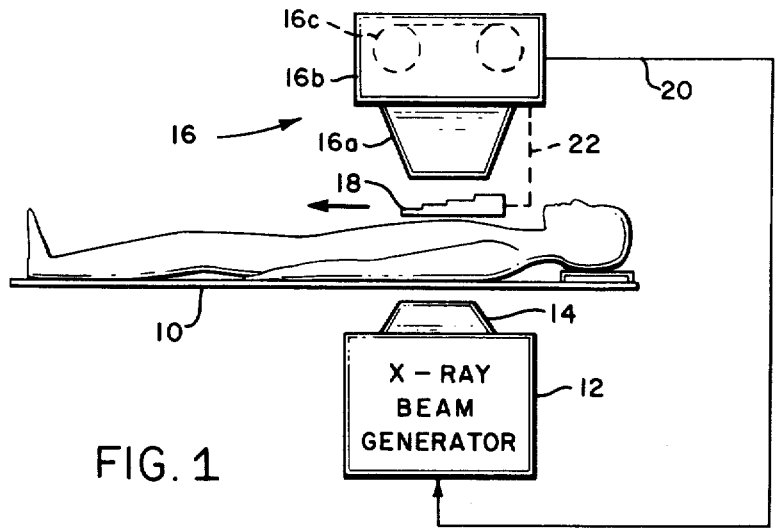
FIG. 1 illustrates a patient positioned for a cinematic radiograph in accordance with the present invention.

Referring to FIG. 1 of the drawings, a patient undergoing radiography shown on a table 10 that is transparent to radiation from a source 12, illustrated as an x-ray beam generator having means 14 for collimating the beam in order to produce parallel rays through the body tissue of the patient of uniform intensity over an area (field) in interest. Placed between the patient and cinematic photographing means 16 is a stepped wedge 18 of known radio-density material, such as steel. The photographing means preferably includes a system 16a for increasing the sensor response to the radiation pattern or image by interposing an active element between the sensor and the image, and supplying power to the active element. A typical arrangement for such an image intensifier includes means for focusing the radiation to be imaged on the photocathode of a cathode ray tube where a photoelectron pattern is produced corresponding to the optical image. This electron pattern is accelerated and focused onto an output phosphor which emits light to produce an intensified image. Cinematic drive mechanism 16b advances photographic film 16c one frame at a time and triggers a shutter to record the image. The x-ray beam generator is electronically synchronized over a line 20 to emit one pulse of energy for each frame. At the same time the wedge 18 is advanced, preferably one step for each frame, using suitable drive means represented by a dashed line 22 that is geared to the cinematic drive mechanism 16b.

Figure 2:
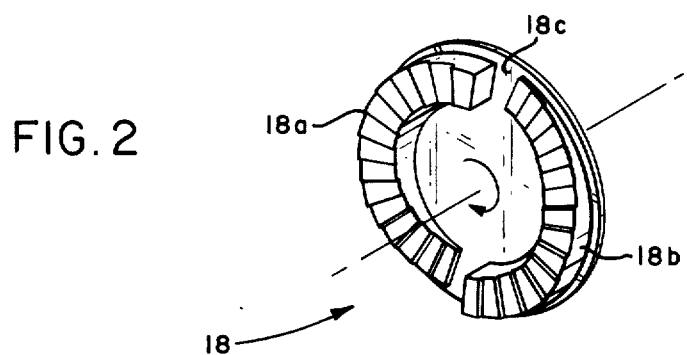
FIG. 2 illustrates one exemplary embodiment of a wedge for use in the system of FIG. 1 in accordance with the present invention.

For simplicity, the stepped wedge is implemented in circular form, with the stepped wedge repeated in each half as shown in FIG. 2. Assuming that the cinematic drive mechanism operates at 30 frames per second, the stepped wedges 18a and 18b on each half of a disc 18c will include fifteen steps for a total of thirty steps per revolution of the disc 18c. The disc 18c itself is transparent to the radiation as is a drive cable and support means (not shown). If the drive cable (represented by the dashed lines 22 in FIG. 1) is rotated at the rate of one revolution per second in synchronism with the cinematic drive mechanism operating at thirty frames per second, a given point in the field of interest overlayed by the stepped wedge will have fifteen successive steps of the wedge for every fifteen frames of the cinematic radiograph.

Figure 3:
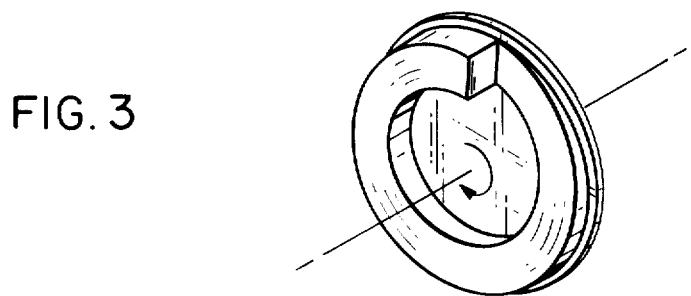
FIG. 3 illustrates a second exemplary embodiment of a wedge for use in the invention.
Figure 4:
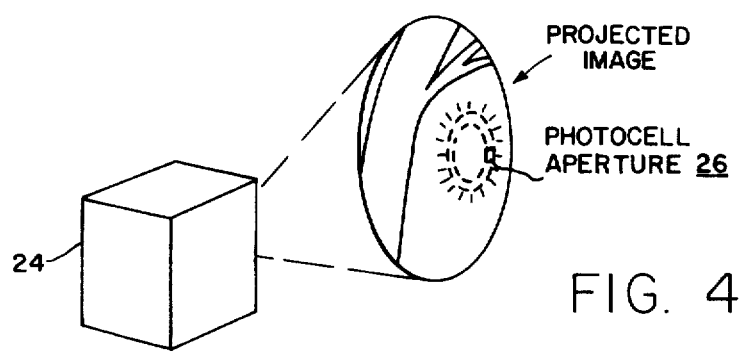
FIG. 4 illustrates the projection of a cinematic radiograph with a photocell having its aperture at a constant position in the field of the radiograph.

It would be possible to construct the wedge as a 360° ramp, as shown in FIG. 3, for as many radio-intensity "steps" for each revolution of the disc as there are exposures per revolution, or as two 180° ramps, each having half that number of radio-density "steps" for the same speed of exposures. If the ramp consists of a linear increase in thickness of the wedge material, synchronization of the disc is not as critical as compared to that for the stepped wedge, since there will be a constant known linear increase in thickness between consecutive steps for a constant disc rotation at any speed. In order to identify specific thicknesses along the ramp wedge, the disc may have "gear" teeth of radio-density material protruding radially so that its position in each frame relative to a particular point in the field can be quickly determined from the presence of the teeth in the image projected in each frame as shown in FIG. 4.

By rotating the circular wedge (or moving a rectilinear wedge) synchronously with pulsed radiographic exposure over the same given point within the radiographic field, x-ray intensity incident to each strip will remain constant over successive frames, so that calibration curves relating transmitted light intensity through cinematic film to thickness of steps can be obtained continuously throughout each film.

Figure 5:
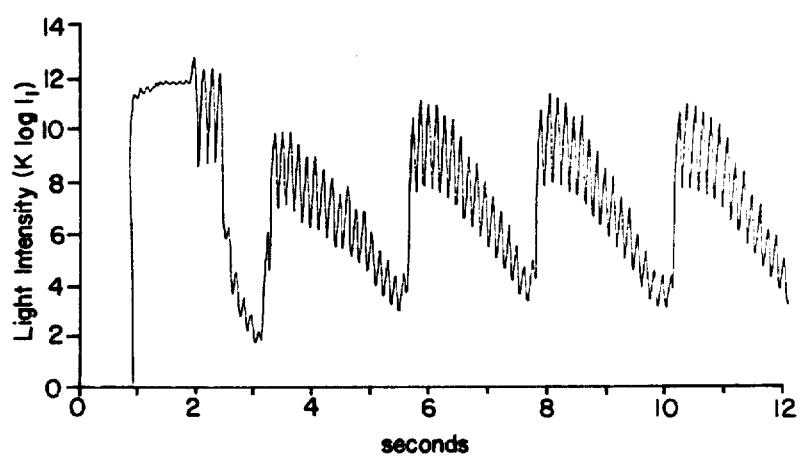
FIG. 5 is a graph of the light intensity measured by the photocell of FIG. 4 as successive frames of a cinematic radiograph are projected.

Once the cinematic film is developed, it is projected, one frame at a time. While the entire field of each frame is projected, only the area of the wedge is of interest during calibration. In that area, a point is selected in the center of a step for positioning a photocell aperture 24, as shown in FIG. 4. Then the intensity of light detected by the photocell for each frame is recorded. FIG. 5 illustrates the response of the photocell as a function of time.

As the wedge image projected rotates over the photocell, a series of peaks and troughs are produced in the output signal of the photocell. Each peak represents light intensity of one step of the wedge image focused from a single frame, while troughs represent a fall in light intensity as the image was blurred between frames. When a ramp wedge of contrast material is used, successive exposures effectively divide the ramp into "steps" of equal increments in thickness, so the output signal is the same. The number of such "steps" per revolution of the ramp wedge could be varied by changing the speed of rotation. It is thus clear that when the stepped wedge of FIG. 2 is used, a series of fifteen peaks establishes the relationship between light intensity and wedge thickness and that when the ramp wedge of FIG. 3 is used, every thirty frames establishes a similar relationship.

In a system having automatic exposure control, the first series of peaks recorded from the initial portion of each cinematic radiograph was markedly different from subsequent series. This characteristic is attributed to the response characteristics of the image intensifier in the automatic exposure mode. Subsequent series of peaks demonstrate a relatively constant amplitude of corresponding peaks from one series to the next. Cinematic radiographic films of twelve patients have been studied and, for each film, three successive series of peaks (omitting the initial portion of each film) were measured. A mean absolute difference of 2.5% ± 1.7% (± 1S.D., n = 360) of maximum peak height between equivalent peaks along each middle series and the corresponding peaks of the two adjacent series was found. Thus, little temporal variation was found, after omission of the initial portion of each film, in the relationship between light intensity and wedge thickness.

As noted hereinbefore, when radiographic exposure of a patient produces a field which is entirely nonuniform in tissue thickness across the object plane, inclusion of a standard, stationary wedge in the field cannot provide meaningful information, since superimposed tissue varies in thickness between wedge steps. This problem is circumvented by the present invention wherein wedge steps of varying thickness are successively superimposed over a single position within the field, and a correlation between wedge step thickness and corresponding light intensity is made over sequential cinematic frames.

Constancy of all radiographic and film variables over the series of frames used should be determined for each application, particularly if an automatic exposure mode is employed. After initial adjustment of the automatic exposure control at the beginning of each film, such constancy is demonstrated in the present invention, wherein the wedge is moved in the field of interest by comparison of a fixed point in the field of interest traversed by steps of the wedge over consecutive series of frames.

Other variations of the wedge may occur to those skilled in the art. For example, the step wedge may be made of radiation transparent material with hollow steps and alternating steps filled with contrast material with steps containing no contrast material. Every other frame is then used to ascertain temporal constancy of radiographic and film variables. Additionally, a film position outside the wedge image may be monitored over sequential frames as a means of determining such temporal constancy.

The rotating circular wedge design and the simple use of a photocell to record light intensity of the wedge image during film projection permit correlation of wedge thickness and corresponding wedge image light intensity over thousands of frames within minutes, as will now be described in more detail with reference to particular hardware selected for experiments.

A type 5 H cadmium sulfide photoconductive cell from Clairex Electronics, Mt. Vernon, N.Y., with a peak spectral response of 5500 Å was used for all measurements of light intensity. Manufacturer specifications included rapid response time, near linear response over a log 0.01 to 100 foot-candle range, and negligible variation of response with light history. Near-linearity was confirmed by measuring light intensity at six different distances from the light source of a Tagarno projector used for all experiments (r = 0.992). Response time for 99 percent peak photocell response was 0.152 sec over a wide range of light intensity. The photocell was connected in parallel with a variable resistance and attached to an Electronics for Medicine Model PHD polarograhic/DC amplifier. A constant voltage of 0.8 to 0.9 volts was applied across the photocell for each study. A continuous display and recording of photocell response to light was then obtained as a measure of the resultant current on an Electronics for Medicine multichannel oscilloscope and recorder. Zero light intensity was obtained by occluding photocell aperture. Reproducibility of individual light intensity measurements was determined by recording 15 different levels of light intensity ten times. A mean variation of 1.0% ± 0.6% was found (n = 150).

For all measurements of light intensity, the photosensitive surface of the photocell was positioned perpendicularly to the direction of light at a constant radius of 51.0 cm from the projector lens (FIG. 4). By mounting the photocell on one limb of a microscope stage, the knob of which was connected to a motor, the photocell could be driven across the direction of light at a constant speed of 0.67 mm/sec.

Preliminary film studies were conducted in the following manner. The projected image of each phantom or artery was focused on the aperture of the photocell. The 1 × 4 mm photocell aperture was aligned so that the 4 mm dimension was parallel to the image long axis as the photocell moved perpendicularly across each image. Since there was a four-fold magnification of projected images over actual dimensions, the 4 mm aperture dimension yielded transverse light intensity scans of cross sections 1 mm in anatomic length. Scans were recorded at a paper speed of 5 mm/sec, and gain was adjusted so that areas under curves were approximately 20 times greater than anatomic dimensions. Reproducibility of recordings was determined by comparing planimetered areas under eight different curves for ten separate runs. Expressed as the ratio of the standard deviation of each curve to the area of the largest curve, a mean 1.5% variation was found.

The light intensity from the projector without film was found to vary as much as ± 14% from a median light intensity over different areas of the field. In order to correct light intensity recordings for this variation, light intensity through a series of three to five unexposed frames of film was measured at the same film positions as those used for measurements of light intensity through exposed frames. The proportional change between levels of light intensity at positions through the unexposed frames was then used as a correction factor by which to adjust levels of light intensity through exposed film.

After the preliminary film studies were made, calibration curves were made from experimental data obtained as follows. A circular stepped wedge was constructed of a gradually increasing number of layers of stainless steel tape, 0.08 mm in thickness, which was technically simpler to utilize than contrast medium. Fifteen increments in thickness, i.e., 1-8, 10, 12, 14, 16, 19, 23, and 28 layers of the tape, were placed in a series and constituted one step wedge. Two such stepped wedges were placed about the circumference of a circular radiation transparent gear (FIG. 2) which was rotated by a constant tension, spring-driven mechanism under a six-inch image intensifier perpendicularly to the direction of x-ray at one revolution per sec. A Philips cine-fluoroscopic unit was used as for routine clinical cinematic angiograms, i.e., all exposures were made on automatic mode with the film selector control programmed for a maximum kV of 125, pulse width 12 msec, and a maximum mA of 200. Either Kodak CFX or Ilford Cinegram F-35 mm cinematic radiographic film was used; films were developed in a Processall (Oscar Fisher Co., New York) at 79° F. for 90 sec for the former and at 75° F. for 101 sec for the latter. A fixed fluoroscopic field was used for each exposure.

At a measured film speed of 33 frames per sec, since each wedge step occupied a width of 1/33 the gear circumference in these experiments, gear movement was recorded on film at a radial speed of one step per frame. Thus, when the wedge image was focused on the photocell as the film moved through the projector, wedge step images were focused one by one on the photocell over sequential frames. For patient studies, the image of an area of end-inspiratory lung field (over which the wedge was overlaid) was focused on the photocell, so that the background image was constant while the images of the wedge steps passed over the photocell during cinematic projection. Areas within the image of the cardiac silhouette were not selected for study of the wedge step images because of constant cardiac motion. A plot of the light intensity of the wedge step images against corresponding step thicknesses established a calibration curve which was then used to relate light intensity elsewhere within the field to contrast material thickness expressed in equivalent units of steel thickness.

For a constant x-ray intensity, $R_o$, incident to thickness of steel, $S_i$, for values of $S_i = 1–8, 10, 12, 14, 16, 19, 23$ and $28$ layers of steel, superimposed over background tissue of thickness $S_t$, $$R_i = R_o e^{-\mu(S_o + S_i)}$$

where $R_i$ is x-ray intensity after traversing background tissues and a discrete thickness of steel, and $\mu$ is the linear attenuation coefficient of steel. $S_o$ is the steel equivalent of the actual tissue thickness $S_t$, and $S_o = (\mu_t/\mu)S_t$, where $\mu_t$ is the linear attenuation coefficient of tissue. Similarly, for a constant ratio of the linear attenuation coefficients of steel ($\mu$) and a contrast material ($\mu_c$), $\lambda_i = (\mu/\mu_c)S_i$, where $\lambda_i$ is contrast material thickness for a given concentration.

Figure 6:
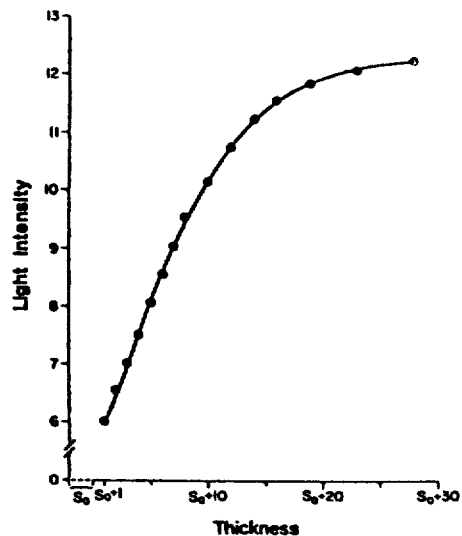
FIG. 6 is a calibration curve developed from the information in the graph of FIG. 5.

A relationship between transmitted light intensity, $I_{ti}$, and $(S_o + S_i)$ can be established empirically by measuring values of $I_{ti}$ over serial frames for corresponding values of $(S_o + S_i)$. The resultant curvilinear plot constitutes a calibration curve shown in FIG. 6.

Points of intersection between one second time lines and transverse light intensity scans across images of contrast-filled vessels were converted manually to values of $(S_o + S_i)$ from the calibration curve to obtain thickness distribution curves. Luminal edges were identified visually as points of greatest change in slope at the beginning and end of light intensity scans.

Figure 7:
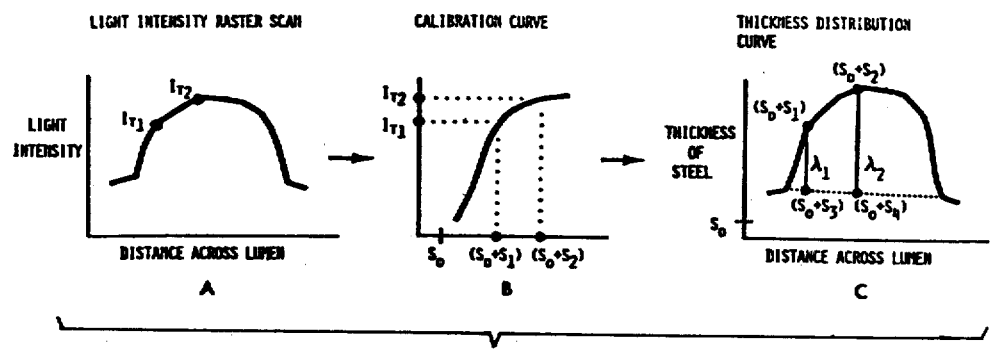
FIGS. 7A, B and C are graphs relating a calibration curve developed in accordance with this invention to relative thickness of contrast material in adjacent arterial cords and relative luminal depths.

From use of the calibration curve, relative thickness of contrast material within adjacent arterial cords and, thus, relative luminal depths may be determined in the following manner. Referring to FIGS. 7A, B and C, if $I_{t1}$ and $I_{t2}$ are light intensities over the projected angiographic image of adjacent arterial cord lengths $\lambda_1$ and $\lambda_2$ of a contrast-filled vessel, $(S_o + S_1)$ and $(S_o + S_2)$ are the corresponding thicknesses of steel determined from the calibration curve. Background tissue thicknesses in equivalent units of steel thickness, $(S_o + S_3)$ and $(S_o + S_4)$, corresponding to $(S_o + S_1)$ and $(S_o + S_2)$ respectively, are estimated by use of the assumption of a linear change in tissue thickness between vessel edges had no contrast material been present.

$S_o$ is eliminated when any two points along the calibration curve are subtracted, and since the proportionality constant between $\lambda_i$ and $S_i$ is eliminated in ratios of $\Delta S_i$, ratios of $\lambda_i$ are calculated directly from ratios of $\Delta S_i$. Similarly, ratios of planimetered areas ($\Sigma \Delta S_i$) under thickness distribution curves can be used to calculate relative cross-sectional areas.

Temporal changes in radiographic and film variables which may occur during the 15 consecutive frames required to establish a calibration curve may lead to errors when applying the curve to any one frame. To ensure constancy of such variables, a calibration curve was selected in each of 12 patients only if the preceding and following curves appeared identical to the calibration curve. The validity of such visual inspection was determined by comparing points along each calibration curve to equivalent points along immediately preceding and following curves.

Spatial variations in beam intensity (heel effect) and in image intensifier gain may lead to errors when applying a calibration curve obtained over lung field to vessels lying within the cardiac silhouette. Reproducibility of the calibration curve between widely separated regions of the radiographic field was therefore studied. Two steel plates of uniform thickness (1 and 1.5 mm) were used to provide a homogeneous background. The entire wedge was filmed within the confines of the field so that pairs of calibration curves could be otained from the developed film 180° apart on the circumference of the wedge. Two calibration curves were recorded from film positions 180° apart over the same series of frames by running the film twice. Potential effects of temporal changes in the calibration curve were thus eliminated. The circumference of the wedge image was divided equally into eight segments, so that four pairs of calibration curves could be obtained.

Differences in beam quality, as the polyenergetic radiation is filtered by either steel, contrast material, or tissue, might result in nonlinear relationships between their respective thicknesses, $S_i$, $\lambda_i$, and $S_t$. A steel wedge and a phantom wedge, filled with various concentrations of meglumine diatrizoate, were filmed together. In order to simulate a range of clinical situations, the phantom wedge was placed over five to ten centimeters of water, while the steel wedge was placed over water zero to four cm less in thickness. For each condition, calibration curves for each pair were obtained and compared.

Two plastic blocks of female casts of a series of metal cylinders were made from a rapidly polymerizing monomer base (Batson's corrosion compound, Polysciences, Warrington, Pa.). One series of metal cylinders for a block measuring $1 \times 2 \times 5$ cm has diameters of 0.51, 0.63, 0.70, 0.91, 1.06, 1.65, 2.35, and 3.08 mm. Metal cylinders used for the second block measuring $1 \times 1 \times 5$ cm had diameters of 1.07, 1.59, 1.98, 2.38, 2.78, 3.18, 3.57, 3.97 and 4.76 mm. The casts were filled with 76% meglumine diatrizoate immediately before each study. Each block of casts was filmed over the cardiac shadow near the anterior border of the beating heart in the RAO view in each of six patients. The long axes of the casts were oriented perpendicularly to x-ray.

Areas under thickness distribution curves across the cylindrical phantoms were planimetered, and ratios of areas were calculated to simulate "percent stenosis:" $100 \times (1 - A_n/A)$, where A corresponded to the cast of the 3.08 mm diameter cylinder in the first block and that of the 3.18 diameter cylinder in the second block, and $A_n$ corresponded to casts of smaller caliber.

Contrast-filled cylindrical phantoms in the two blocks were similarly studied in cinematic radiographs taken over a homogeneous background consisting of two steel plates of uniform thickness of 1 and 1.5 mm. Pincushion distortion was estimated in this study by comparing cylindrical phantom diameters at the center to those at the periphery of the angiographic field.

Percent stenosis was determined of a right coronary artery during mid-injection of meglumine diatrizoate in a patient undergoing routine coronary arteriography by comparing the area under the thickness distribution curve of the stenotic segment to that of the adjacent proximal segment. Thirty degree RAO and 60 degree LAO angiographic views were studied and compared.

By projecting film at a constant speed of approximately seven frames per sec, calibration curves were recorded continuously as a series of peaks throughout each film similar to that shown in FIG. 5. A continuous calibration curve was constructed by drawing a best-fit smooth curve across successive peaks. If slight asynchrony occurred between film exposure and circular wedge speeds, greater or fewer than 15 peaks were recorded per steel array; the baseline along a single series of changes in light intensity was then divided into 15 equal segments, and the intersection of each of the segments at its midsection and best-fit curve was used to identify the light intensity for the corresponding thickness of steel.

A mean absolute difference of 2.5% ± 1.7% (± 1S.D., n = 360) of peak curve height was found between equivalent points along each calibration curve and corresponding curves immediately preceding and following each calibration curve used in the 12 patients studied. Temporal changes in radiographic and film variables which affect the relationship between film gray scale and wedge thickness therefore appeared small.

In studies of reproducibility of the calibration curve over widely separated areas of the cinematic radiographic field, a mean absolute difference of 4.4% ± 2.2% (± 1S.D., n = 60) was found between equivalent points of the four pairs of calibration curves.

In comparison of calibration curves obtained with steel and contrast material superimposed over various thicknesses of water, an empirically derived constant was determined which, when applied to steel thickness values, resulted in a mean absolute difference in thickness between the two materials of 1.2% of peak steel thickness when equivalent light intensity values were matched (n = 150).

Using cylindrical phantoms over cardiac silhouette, seventy-two cross-sectional area ratios were determined from 84 thickness distribution curves and expressed as percent stenosis of the cast made from either the 3.08 or 3.18 mm diameter cylinder, depending upon which block of casts was studied. Six values for each of 12 known percent stenoses were obtained, representing six separate studies with each of the two blocks of casts. When measured cross-sectional area ratios were compared to known values, the range of ± 1S.D. for the 12 means was 0.9 to 8.0%. A mean error of 3.6% ± 3.4% between measured and known ratios was found (r = 0.981).

Relative diameters of the cylindrical phantom images were determined by measuring the horizontal distance between the luminal edges identified in the 84 thickness distribution curves. Extrapolation of cross-sectional area ratios from diameter measurements resulted in a mean error, between measured and known ratios, of 7.6% ± 6.5%, which was significantly greater than the mean error of area ratios determined directly from thickness distribution curves in a t-statistic evaluation of paired data (P < 0.005).

From each film of six patients, three additional thickness distribution curves were obtained across larger cylindrical phantoms, corresponding to cylinders 3.57, 3.97 and 4.76 mm in diameters. When used in denominator for determining percent stenosis, the planimetered cross-sectional area of the largest cylinder produced a wider range of ± 1S.D. for the 12 means, 1.2 to 11.2%. The largest variation occurred when cross-sectional areas of any two of the three larger phantoms were compared.

Determination of thickness distribution curves and percent stenosis of cylindrical phantoms over a homogeneous background yielded a mean difference of 2.9% ± 2.2% between measured and known values of 23 ratios (r = 0.989).

An 83% stenosis in the RAO view and a 79% stenosis in the LAO view of the right coronary artery of a patient undergoing routine coronary arteriography was found.

Pincushion distortion produced a mean 6.7% magnification of cylindrical phantom diameter (n = 7) at the periphery relative to the center of the radiographic field. Since each block of casts was positioned centrally for all studies and occupied approximately 25% of the field diameter, this effect was small.

Utilization of all the image information between luminal edges should increase the accuracy of cross-sectional area estimates beyond that of estimates derived from edge identification alone. When cross-sectional areas of cylindrical lumens are extrapolated from diameter measurements alone, fractional errors in the latter are doubled. The significance of this fact is illustrated by the findings in the present study. Diameters of the cylindrical phantom images were measured to within ± 120 microns of known values, and greater accuracy is not readily obtainable. However, the error of cross-sectional area ratios derived from diameter measurements was 7.6% compared to a 3.6% error when area ratios were determined directly.

Because of the focal nature of the atherosclerotic process, nonaxisymmetric reductions in luminal cross-sectional area are common. The error associated with edge-dependent area ratios may therefore become greatly magnified in studies of atherosclerotic vessels, while calculations of area ratios from knowledge of relative thickness of contrast material are likely to be independent of luminal geometry.

In order to extract luminal cross-sectional area information, two separate film locations must be studied: the vessel image within the myocardial shadow in a single frame and the rotating wedge image overlying lung field over multiple frames. The effects of film location and time on the calibration curve are therefore potentially important. However, field location-dependent variation in the calibration curve, primarily as a result of anodal heel effect, was found to be small over a field of homogeneous thickness. Likewise, little temporal variation in the calibration curve was found when selection was based on similarity to curves recorded immediately before and after the calibration curve.

Variations in spectral hardening which may occur between combinations of soft tissue and either steel or contrast material did not appear to be an important consideration. The relative thicknesses of steel and contrast material were linearly related along the abcissas of paired calibration curves despite differences in initial beam filtration by graded thicknesses of water. It should be noted, however, that variation in tube potential, as occurs during automatic exposure control in some radiographic systems, the choice of other materials might result in nonlinearitities between the thicknesses of any two materials.

Additional studies may be required to define errors associated with measurements of relative cross-sectional areas of adjacent coronary artery segments. Correlation of orthogonal radiographic views will be necessary to correct for oblique angles of x-ray vessel orientation. If significant contrast material concentration gradients are present between adjacent segments, despite selection of frames from midinjection of an adequate injection of contrast material, multiple frame analysis may be necessary to approach the accuracy of the phantom studies. However, artifactual variations in videodensitometric blood flow measurements as a result of contrast material layering only at the tail end of bolus injection have been noted. Visual inspection of a coronary angiogram should be sufficient to select segments for study which are free of overlapping branches and radio-dense calcium within the arterial wall.

Emphasis has been placed on extraction of luminal cross-sectional area information from coronary cinematic angiograms. However, the rotating wedge technique is potentially applicable to rapid sequence radiography in general, when it is necessary to calibrate film gray scale against thickness of objects within a field which is nonuniform in x-ray attenuation throughout the object plane. By focusing the rotating wedge image on a photocell, one calibration curve cna be recorded every three seconds continuously throughout a cinematic sequence, so that dynamic changes in the shape of the curve may be studied quickly and easily.

The present invention, in addition to calibrating the gray scale of film, can also be used to calibrate the gray scale of any means of recording the image on the output phosphor of an image intensifier, such as videotape and digital photoelectronic recordings.

For any radiographic system employing a source of x-rays and a detector, such as an x-ray exposure meter or a film-screen combination, a stationary wedge can be used to standardize the intensity of the exposure by measuring the detector response after the x-ray beam has penetrated each step of a wedge of known graded thicknesses. Such standardization has been limited to situations wherein the radiographic field is homogeneous in thickness throughout the object plane. When the radiographic field is nonuniform throughout the object plane, the rotating wedge technique can be used to standardize exposures by determining the detector response at one position within the radiographic field over sequential exposures.

What is claimed is:

1. A method for calibrating rapid sequence radiography comprised of the steps of
   positioning a movable wedge of radio-dense material in the field of interest between an x-ray source and cinematic photography means,
   moving said wedge in synchronism with said cinematic photography means to place successive portions of said wedge over a constant position in said field to change the thickness of radio-dense material of said wedge over said position for each frame of said cinematic radiography,
   recording on cinematic film each successive frame of said radiography,
   developing said film,
   projecting each successive frame of said developed film,
   detecting the intensity of light at a constant position of each projected frame corresponding to said constant position of said wedge in said field,
   from the intensity data developing a calibration curve relating light intensity to thickness of said wedge in said field of interest, and
   from said calibration curve translating intensity data at any position within said field into equivalent thickness of said wedge.

2. A method as defined in claim 1 wherein said wedge varies in thickness in steps and positioning said wedge is carried out by advancing it one step length for each frame.

3. A method as defined in claim 2 wherein said stepped wedge is circular and mounted on a radiation transparent disc, and motion of said wedge is achieved by rotating said wedge at a speed synchronized with said cinematic photographing means.

4. A method as defined in claim 1 wherein said wedge is a ramp, and positioning said wedge is carried out by moving it a predetermined length for each frame.

5. A method as defined in claim 4 wherein said ramp wedge is circular and mounted on a radiation transparent disc, and motion of said wedge is achieved by rotating said disc.

6. Apparatus for calibrating cinematic radiography comprised of
   a radiation generator,
   cinematic photographing means positioned to produce a cinematic radiograph, one frame at a time in succession of a field of interest in a patient,
   a wedge of known radio-dense material positioned in said field of interest between said patient and photographing means,
   means for moving said wedge in synchronism with said cinematic photography means to place a portion of said wedge over a constant position in said field to change the thickness of radio-dense material of said wedge for each frame of said cinematic radiography,
   means for projecting each successive frame of said cinematic radiography, and
   means for detecting the intensity of light at a constant position for each projected frame corresponding to said constant position of said wedge in said field, whereby a calibration curve relating light intensity to thickness of said wedge in said field of interest may be developed.

7. Apparatus as defined in claim 6 wherein said wedge varies in thickness in steps, and said means for moving said wedge advances said wedge one step length for each frame.

8. Apparatus as defined in claim 7 wherein said stepped wedge is circular and mounted on a disc, and said means for moving said wedge rotates said disc at a speed synchronized with said cinematic photographing means.

9. Apparatus as defined in claim 6 wherein said wedge is a ramp, and said means for moving said wedge advances said wedge a predetermined length for each step.

10. Apparatus as defined in claim 9 wherein said ramp wedge is circular and mounted on a radiation transparent disc, and said means for moving said wedge rotates said disc at a speed synchronized with said cinematic photography means.

* * * * *